United States Patent [19]

Matsuda et al.

[11] Patent Number: 5,139,949
[45] Date of Patent: Aug. 18, 1992

[54] ANTI-MICROBIAL AND ANTI-NEMATODE COMPOSITION, AND CHITINOLYTIC MICROORGANISM FOR PRODUCING THE SAME

[75] Inventors: Hideyuki Matsuda, Matsue; Youzi Omura, Izumo, both of Japan

[73] Assignee: San-in Kensetsu Kogyo K.K., Japan

[21] Appl. No.: 636,103

[22] Filed: Dec. 31, 1990

[51] Int. Cl.$^5$ .......................... C12N 1/22; C08B 37/08; A61K 31/73
[52] U.S. Cl. .................................... 435/252; 435/274; 514/55; 47/58
[58] Field of Search ................... 514/55; 435/252, 274; 47/58

[56] References Cited

U.S. PATENT DOCUMENTS

| | | | |
|---|---|---|---|
| 4,751,081 | 6/1988 | Suslow | 424/93 |
| 4,940,840 | 7/1990 | Suslow | 800/205 |

FOREIGN PATENT DOCUMENTS 2-152904  6/1990  Japan .................................... 435/252

OTHER PUBLICATIONS

Molise Em. Chitinolysis by Serratiae, Int J of Systematic Bactertiology Jul. 73, pp. 278–280, vol. 23, No. 3.
Mowlah, A. H. Microflora in the Alimentary Tract of Gray Mullet-V, Bulletin of the Japanese Society of Scientific Fisheries 45 (10) 1313–1317 (1979).

*Primary Examiner*—Ronald W. Griffin
*Assistant Examiner*—Ralph Gitomer
*Attorney, Agent, or Firm*—Parkhurst, Wendel & Rossi

[57] ABSTRACT

An anti-microbial composition or an anti-nematode agent including chitosan which is obtained by decomposing chitin with a strain of Enterobacter G-1, which was deposited in the Fermentation Research Institute, Agency of Industrial Science and Technology, Japan, or including a culture body which is obtained by cultivating the above strain of Enterobacter G-1 on a culture medium containing chitin.

6 Claims, 1 Drawing Sheet

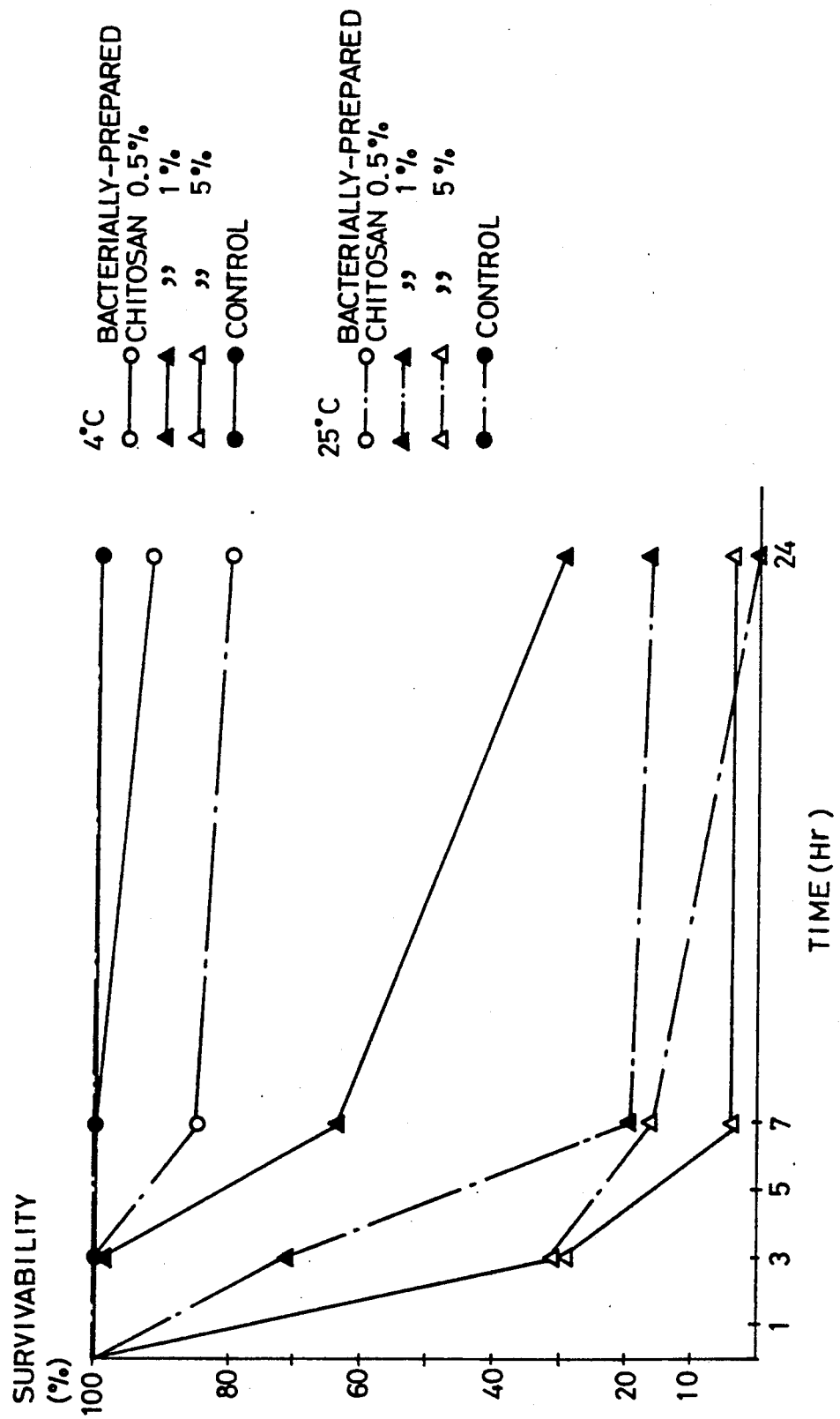

ND ANTI-NEMATODE
ANTI-MICROBIAL AND ANTI-NEMATODE COMPOSITION, AND CHITINOLYTIC MICROORGANISM FOR PRODUCING THE SAME

BACKGROUND OF THE INVENTION

1. Field of the Invention

The present invention relates in general to a pharmaceutical material or composition having antimicrobial or antibacterial, and anti-nematode activities, and strains of chitinolytic microorganisms or bacteria for producing such a pharmaceutical composition. More particularly, this invention is concerned with an anti-microbial composition or anti- nematode agent, which includes as an effective component chitosan that is obtained by decomposing chitin from the integument of crustacea, such as a crab shell, while utilizing a culture of the chitinolytic microorganisms, or which includes a culture liquid that is obtained by cultivating the chitinolytic microorganisms.

2. Discussion of the Prior Art

In recent years, the integument of crustacea, such as a crab shell, has been chemically treated to provide chitosan which serves as a very useful substance. In the conventional chemical treatment, the integument of crustacea (crab shell) is initially decalcified, and the decalcified integument is then deproteinized with a protease or 1% alkali solution to provide chitin. Then, chitin obtained was deacetylated in a 40% aqueous alkaline solution to thereby provide chitosan. The thus obtained chitosan is one of rare natural basic polysaccharides, and is used as a drainage or sewage flocculant, for example. It is recognized that chitosan is also useful when applied to a thread used for surgical operations, an artificial skin or a fertilizer.

SUMMARY OF THE INVENTION

Having the above recognition, the inventors named in this application made an extensive research in an effort to find in nature the microorganisms which have high ability of decomposing chitin, in particular, chitin present in the integument of crustacea, and high ability of producing chitosan and various kinds of chitinolytic enzymes. The research resulted in finding that a strain of chitinolytic bacteria which belongs to a species of Enterobacter, namely, a strain of Enterobacter G-1, can be used for decomposing chitin into chitosan, which has excellent anti-microbial and anti-nematode effects or activities. The inventors also found that a culture liquid which is obtained by culturing the chitinolytic bacteria on a chitin medium has similar anti-microbial and anti-nematode activities.

It is therefore an object of the present invention to provide a pharmaceutical composition which includes a pharmaceutically effective component in the form of chitosan that is prepared by using chitinolytic bacteria, and which has anti-microbial and/or anti-nematode activities.

A second object of the invention is to provide a bacterium which provides such a pharmaceutical composition.

The first object may be achieved according to one aspect of the present invention, which provides an anti-microbial or anti-nematode composition including chitosan which is obtained by decomposing chitin with a strain of Enterobacter G-1. The strain of Enterobacter G-1 so named is deposited in the Fermentation Research Institute, Agency of Industrial Science and Technology located at 1-3, Higashi 1 chome, Tsukuba-shi, Ibaraki-ken, 305, Japan, under deposit number FERM BP-3140 on the date of Nov. 14, 1988.

The second object may be achieved according to another aspect of the invention, which provides a strain named "Enterobacter G-1" deposited as indicated above, which is a chitinolytic bacterium capable of providing a composition as defined above.

The strain of bacteria named "Enterobacter G-1" according to the present invention is isolated as a microorganism which is able to decompose chitin present in the integument of crustacea such as a crab shell, into chitosan which has excellent anti-microbial or anti-nematode activities. The chitosan obtained from chitin by using the present chitinolytic bacteria (Enterobacter G-1) serves as an effective component of an anti-microbial composition or anti-nematode agent. This composition or agent containing chitosan exhibits an excellent anti-microbial effect with respect to crown gall of grapes, crown gall of roses, sheath blight of rice caused by rhizoctonia, Phoma wasabiae Yokogi of wasabi (Japanese horseradish), and other plant diseases, and an excellent insecticidal or anti-nematode effect with respect to nematodes such as pine tree nematodes.

BRIEF DESCRIPTION OF THE DRAWING

In the accompanying drawing, the single figure is a graph showing an effect of chitosan obtained by using chitinolytic bacteria according to the present invention, when the chitosan was used as an insecticide for killing pine tree nematodes.

DETAILED DESCRIPTION OF THE INVENTION

A microorganism, which is a species of the chitinolytic bacteria according to the present invention, was named Enterobacter G-1. A strain of the chitinolytic bacteria was extracted from water which is obtained in the site of Gessho-ji (temple) located at Matsue-shi, Shimane-ken, Japan. The bacteria present in the water was cultured successively at ten times in about five months, on a culture medium containing only a decalcified crab shell powder and 0.2% $K_2HPO_4$, in order to induce chitin- o decomposing or chitinolytic activity of the bacteria. The strain of the bacteria was isolated from the water described above, and was deposited on Nov. 14, 1988, in the Fermentation Research Institute, Agency of Industrial Science and Technology located at 1-3, Higashi 1 chome, Tsukuba-shi, Ibaraki-ken, 305, Japan, under deposit number FERM BP-3140. The chitinolytic bacterial has the following mycological characteristics and properties:

(I) Morphological Characteristics

This strain of bacteria belongs to the Gram-negative species ($0.7 \sim 1.2 \mu m \times 1.0 \sim 1.5 \mu m$) of Bacillus, and has no spores.

(II) Culture Characteristics on Different Media (1) Broth medium

A cream-colored colony having a smooth surface and a circular periphery spread over the medium. A slight degree of convexity was found on the colony.

(2) Colloidal chitin agar

A white colony having an undulated surface with small concave and convex portions spread over the agar, and the colony extends down toward the lower surface of the agar. A transparent clear area was formed around the colony after the bacteria were cultured at 30° C. for a day.

(III) Physiological Properties (1) Growth temperature range

[Cultivation by a liquid shaking method]

15°-33° C. (optimum growth temperature: 26° C.)

[Colloidal chitin agar]

16°-50° C. (optimum growth temperature: 30° C.)

[Days required for producing a clear area]

|  |  |
|---|---|
| 16° C. | 2 days |
| 30° C. | 1 day |
| 37° C. | 1 day |
| 42° C. | 4 days |
| (2) Growth pH range | 4-9 |
| (3) Nitrate reduction | Positive |
| (4) $H_2S$ production | Positive |
| (5) Indole formation | Negative |
| (6) V-P test | Positive |
| (7) O-F test | Fermentative |
| (8) Methyl red test | Negative |
| (9) Catalase | Positive |
| (10) Oxidase | Negative |
| (11) Urease | Negative |
| (12) Acid and gas production from carbohydrates | |

(IV) Identification

Judging from the above-described characteristics and properties of the present strain of bacteria, the strain appears to belong to a species of Enterobacter, according to "Bergey's manual of systematic biotechnology", Vol. 1, and "Classification and Identification of Microorganisms", Vol. 2, Takeharu Hasegawa, Gakugei Publishing Company, Japan. However, the properties of the present strain in respect of the acid and gas production from carbohydrates do not completely coincide with those of any known strain of Enterobacter given in the above-identified publications. Further, with respect to H,S production, the present strain is positive, contrary to any known strain of Enterobacter. Therefore, the present strain was recognized as a new strain, and was named "Enterobacter G-1".

(V) Cultivation of Bacteria

The strain of Enterobacter G-1 may be cultivated by an ordinary method used for cultivating Actinomycetes. For assuring chitinolytic activities of the bacteria, chitin such as colloidal chitin is used as a major carbon source of a culture medium, in combination with other suitable known carbon sources. As a nitrogen source of the medium, ammonium salt, nitrate, yeast extract and peptone may be used alone or in combination. As a phosphorus source, phosphate may be used. Other sources such as alkali metal salt, magnesium sulfate, iron sulfate, zinc sulfate and manganese chloride may be added as needed.

While a solid culture medium may be used, it is desirable to use a liquid culture medium generally used for producing yeast. An example of a preferred liquid culture medium has a composition at pH 7.0 which consists of: 4g of colloidal chitin; 0.7g of $K_2HPO_4$; 0.3g of $KH_2PO_4$; 0.5g of $MgSO_4.5H_2O$; 0.01g of $FeSO_4.7H_2O$; 0.001g of $ZnSO_4$; 0.001g of $MnCl_2$; 0.25g of yeast extract; 0.25g of peptone; 15g of agar; and 1000ml of distilled water. Generally, the growth of the present strain on such a culture medium takes place at a temperature between 20° C. and 40° C.

According to the present invention, the strain of Enterobacter G-1 is used for decomposing chitin which occurs in the integument of crustacea such as crab shells, into chitosan. Described specifically, the integument of crustacea is decalcified in a medium containing a suitable acid such as hydrochloric acid. In this treatment, CaCO present in the integument is dissolved out into the medium and removed from the thus decalcified integument, which is obtained in a powder state. The decalcifying treatment described above reduces the whole volume of the integument to thereby facilitate handling thereof, and eliminates the necessity of treating calcium which would otherwise be present in a culture tank in a subsequent step in which the integument is processed by the chitinolytic bacteria cultivated in the tank. At the same time, blackened microorganisms living in the integument may be killed by this decalcifying treatment.

The powder of the decalcified integument of crustacea is dispersed in a suitable medium such as water, and the obtained dispersion liquid is introduced in a suitable bioreactor in which the integument is processed by using the strain of chitinolytic bacteria according to the present invention. More specifically, suitable components similar to those of the liquid culture medium indicated above are added as needed to the dispersion liquid in which the integument powder is dispersed, to provide a culture medium for the cultivation of the chitinolytic bacteria. On this culture medium which is maintained at a temperature between 20° C. and 40° C., the strain of the present chitinolytic bacteria is cultivated for 10-15 days while the liquid is stirred, so that the integument of crustacea is processed so as to produce chitosan and other useful substances.

Various conditions for the above microbial treatment, such as percentage of the amount of the integument with respect to the liquid accommodated in the bioreactor, the amount of the chitinolytic bacteria added to the culture medium, and cultivation temperature and time, are suitably determined so that the amount of chitosan thus produced in the culture medium is maximized.

The processing of the integument of crustacea with the chitinolytic bacteria will be hereinafter described in more detail. The present strain of bacteria which is grown on the culture medium functions to deproteinize the integument, in particular, decalcified integument, so as to produce chitin. The chitin from the integument is further processed by the chitinolytic bacteria to produce chitinase, chitindeacetylase and chitosanase, and to produce chitosan. The present strain of bacteria is effective to lower the molecular weight of the produced chitosan andchitin. Then, the cultivation of the bacteria is stopped when the amount of chitosan and other reaction products (enzymes) as specified above is at its maximum. These reaction products are isolated from the culture liquid containing the culture of the bacteria, by differential centrifugation, for example. The isolated products are then purified. By this differential centrifugation, the culture liquid is separated into a supernatant liquid (culture filtrate) and a precipitate. From the precipitate, a powder of chitosan is extracted. From the supernatant liquid, useful decomposing enzymes such as chitinase and chitosanase are extracted by ultrafiltration, chitin affinity chromatography, isoelectric focusing, or other known methods.

While the reaction products are isolated after the completion of the cultivation of the bacteria in the culture tank in the above method, the culture liquid may be removed from the tank from time to time during an intermittent processing of the integument of crustacea. The removed culture liquid is then separated in the manner as described above to provide chitosan and decomposing enzymes. More specifically, the culture liquid is removed from the tank after a certain period of cultivation of the bacteria, and then subjected to a filtering operation by a filter capable of blocking whole molecular weight exceeds 200,000, so as to filter out a mixture of the bacteria, chitin and chitosan. Chitosan is separated from the mixture, and the bacteria and chitin are returned back into the culture tank. With a suitable amount of the decalcified integument of crustacea such as crab shells being added to the culture tank as needed, the processing of the integument by the bacteria may be re-started in the tank.

Chitosan obtained in the manner as described above has excellent anti-microbial and anti-nematode (insecticide) effects or activities, and may therefore be used as an effective component of an anti-microbial composition or an anti-nematode agent, which is prepared as desired according to a known recipe. Further, since the present strain of bacteria (Enterobacter G-1) is grown on a culture medium containing chitin, such as colloidal chitin agar, to provide chitosan, a culture liquid (culture body) obtained by cultivating the bacteria on such a chitin medium also has similar anti-microbial and anti-nematode effects. Thus, the culture liquid per se may be also used to prepare an anti-microbial composition or an anti-nematode agent.

Inventors' research and analysis up to the present do not reveal a sufficiently clear reason for the effects or functions of the chitosan obtained by using the present chitinolytic bacteria, namely, the functions of preventing proliferation of pathogenic bacteria and activating plant cells. However, it is presumed that the functions result from the following, which conforms with results of experiments.

Namely, cells of a plant which exists in a contaminated soil are likely to be subjected to infection with pathogenic bacteria, invasion of nematodes, and eating by insects, which result in disordered physiological functions, nutrition lesion and undergrowth of the plant. Eventually, the plant withers up or dies. On the other hand, the following four phenomena or reactions occur in an active soil to which chitosan is applied. First, the applied chitosan is hydrolyzed by co-existing microorganisms, and is developed into low-molecular weight, water-soluble oligosaccharide of chitosan, which is introduced into the plant cells to promote the transcription from DNA to RNA. As a result of this first phenomenon, the plant cells vigorously perform synthesis of protein, which leads to promotion of biosynthesis of enzymes such as chitinase and chitosanase, and antibacterial substances such as phytoalexin. This is the second phenomenon. Then, these enzymes lyze or decompose the cell walls of the pathogenic bacteria, and phytoalexin, oligosaccharide of chitosan and other substances enter the cells of the pathogenic bacteria so as to prevent the trascription from DNA to RNA and proliferation of the pathogenic bacteria. This is the third phenomenon. As a result of the third phenomenon, i.e., lysis of the cell walls of the pathogenic bacteria, there are newly formed oligosaccharide of chitosan, which functions to promote activation of the plant cells. The thus formed oligosaccharide of chitosan and various enzymes are supposed to attack nematodes to prevent their growth. This is the fourth phenomenon. While the series of reactions described above occur in the presence of chitosan as a starting material, the major role for permitting these reactions is played by the co-existing microorganisms in the soil, which cooperate with each other to decompose chitosan into oligosaccharide of chitosan. In this respect, it is noted that the chitosan is produced from the integument of crustacea by utilizing the chitinolytic function of the present strain of bacteria named Enterobacter G-1.

To clarify the concept of the present invention, some examples of the present invention will be given below. However, it is to be understood that the invention is not limited to the details of the illustrated examples, and that the invention may be embodied with various changes, modifications and improvements, which may occur to those skilled in the art, without departing from the spirit and scope of the invention.

It is also to be understood that the percentage used in the following examples is expressed by weight, when appropriate.

Preparation of Chitosan by Microbial Treatment

Initially, a 30 liters of culture liquid at pH 7.0 was prepared, which contained: 400g of decalcified crab shell powder which was decalcified by 1% HCl solution; 0.025% of peptone; 0.2% of $K_2HPO_4$; and a 700 ml culture of the above-identified strain of Enterobacter G-1. The culture liquid was maintained at 30° C. for 14 days in a reciprocal shaker. Thereafter, the culture liquid was subjected to differential centrifugation, to obtain a precipitate whose dry weight was about 200g. It was revealed from an analysis utilizing infrared absorption spectrum that the precipitate was a mixture of about 50 ~60% deacetylated crude chitin and chitosan, and other substances. By treating this mixture with acetic acid, there were obtained 48% (about 90g) of acetic-acid-insoluble crude chitosan and 52% (about 105g) of acetic-acid-soluble components. The acetic-acid-soluble components contained acetic-acid-soluble protein derived from chitosan and crab shell combined protein.

On the other hand, the supernatant liquid or culture filtrate obtained by the above-described differential centrifugation corresponds to 200g of the decalcified crab shell as dissolved in the liquid, which is considered to contain soluble, low-molecular weight components of chitin and chitosan, for example, that is, crude N-acetylglucosamine oligosaccharide, glucosamine oligosaccharide, and partially-acetylated glucosamine oligosaccharide, for example.

The activities of enzymes produced as a result of the cultivation as described above were assayed in the following manners. First, the chitinase activity was measured of a mixture which contained: 0.5ml aqueous solution containing 0.5% of colloidal chitin; ml of 0.1M citric acid-0.2M disodium hydrogenphosphate buffer (pH 7.0); and 0.5 ml of the culture filtrate (crude enzyme solution) to make a final volume of 2.0 ml. The prepared 2.0 ml mixture was incubated at 30° C. for 30 min., and then boiled at 100° C. for 5 min. to nullify the enzyme activity. The amount of the thus obtained reducing end-group was determined by the SCHALES modified method. One unit of the chitinase activity was defined as the amount of chitinase that produces reducing sugar equivalent to 1 mol of N-acetylglucosamine.

The chitosanase activity was measured of a mixture which contained 0.5 ml of an aqueous solution (pH 6.0) containing 1% of colloidal chitosan and 0.5 ml of the culture filtrate indicated above. The mixture was incubated at 30° C. for 30min., and then boiled at 100° C. for 5 min. to nullify the enzyme activity. Thereafter, the amount of the released reducing sugar was determined by the SCHALES modified method. One unit of the chitosanase activity was defined as the amount of chitosanase that produces 1 mol of glucosamine per minute.

The chitindeacetylase activity was measured of a mixture which contained: 0.5ml of an aqueous solution containing 0.5% of colloidal chitin; 1 ml of 0.1 M citric acid-0.2M disodium hydrogenphosphate buffer (pH 7.0); and 0.5 ml of the culture filtrate (enzyme solution), to make a final volume of 2.0 ml. The mixture was incubated at 30° C. for 30min., and was then boiled at 100° C. for 5 min. to nullify the enzyme activity. Then, NH,-group produced by the incubation was measured by colloidal titration.

It was revealed in the above example that a maximum of approximately 210 g of acetic-acid-soluble components containing chitosan were produced, and several grams of N-acetylglucosamine and glucosamine were also obtained. The yield of producing the acetic-acid-soluble components containing chitosan from chitin was about 52%. In this case, 180 to 300mg of enzymes such as chitinase and chitosanase were produced as enzymatic protein. The produced chitinase and chitosanase amounted to 360–600 units if one unit is defined as the amount of enzyme for cleavage of 1 μmol of β-1, 4-glucoside bond per minute. Similarly, 120 to 80 mg of chitindeacetylase was produced as enzymatic protein, which amounted to 210–300 units of enzyme.

Test of Bacterially-prepared Chitosan and Culture Liquid for Anti-microbial Activity Initially, there were prepared agar media to which were applied 0.1%, 0.5% and 1% of bacterially-prepared chitosan that was obtained by using the chitinolytic bacteria, Enterobacter G-1, according to the present invention, and an agar medium as a reference medium to which no chitosan was applied. As comparative examples, there were also prepared agar media to which chemically-prepared chitosan, such as colloidal chitosan, powdered chitosan and colloidal chitin, were applied in the above-indicated concentrations. On the agar media containing the bacterially-prepared chitosan, and on the comparative agar containing chemically-prepared chitosan as indicated above, there were planted diseased plants such as grape vine suffering from crown gall, rice suffering from sheath blight caused by rhizoctonia or wasabi suffering from Phoma wasabiae Yokogi, or pathogenic microbes of the diseases.

First, the test was conducted to examine anti-microbial activities of the various kinds of chitosan as indicated above, with respect to pathogenic microbes (Agrobacterium tumefaciens) of the crown gall of grapes. To prepare culture media, each of colloidal chitosan, powdered chitosan, bacterially-prepared chitosan and colloidal chitin was added in the different concentrations to an ordinary agar medium (pH 7.0) as the control medium which contained 5g of meat extract, 5g of sodium chloride, 10g of peptone, 15g of agar-agar and 1000ml of water. The pathogenic microbes which had been grown on a liquid medium were applied to each of the prepared culture media, and grown or cultured on the above culture media at 30° C. for three days. Then, the number of the pathogenic microbes remaining on each culture medium was measured. The result of the measurement was indicated on TABLE 1 given below.

The same test was conducted to examine anti-bacterial activities of chitosan, with respect to pathogenic microbes of the crown gall of roses. The result of the test was similar to that obtained in the above test with respect to the crown gall of grapes.

TABLE 1

|  |  | Dilution (time) | Number of microbes |
|---|---|---|---|
| Control medium |  | $10^5$ | 231 |
| Colloidal chitosan media | 0.5% | $10^5$ | 106 |
|  | 1.0% | $10^5$ | 91 |
| Powdered chitosan media | 0.5% | $10^5$ | 94 |
|  | 1.0% | $10^5$ | 83 |
| Bacterially-treated chitosan media | 0.5% | $10^4, 10^3$ | 0 |
|  | 1.0% | $10^4, 10^3$ | 0 |
|  | 5.0% | $10^4, 10^3$ | 0 |
| Colloidal chitin | 1.0% | $10^5$ | 92 |

The next test was conducted to examine anti-bacterial activities of the above-indicated kinds of chitosan, with respect to pathogenic microbes of Phoma wasabiae Yokogi of wasabi (Japanese horseradish). To prepare culture media, each of colloidal chitosan, powdered chitosan, bacterially-prepared chitosan and colloidal chitin was applied in the different concentrations to an ordinary agar medium similar to that used for the above test, which served as the control medium. The pathogenic microbes were planted on nine spots of each culture medium, and were cultured on the medium at 30° C. for eight days. The anti-bacterial activity of each kind of chitosan was determined based on the average diameters of colonies of the microbes on the nine spots of the culture medium. The result of this test was indicated on TABLE 2 given below.

TABLE 2

|  |  | Diameter of Colony (cm) | | | |
|---|---|---|---|---|---|
|  |  | 3 days | 5 days | 8 days | 12 day |
| Control medium |  | 0.3 | 1.0 | 1.5 | 1.8 |
| Colloidal chitosan media | 0.5% | 0.4 | 1.0 | 1.1 | 1.2 |
|  | 1.0% | 0.3 | 0.7 | 0.8 | — |
| Powdered chitosan media | 0.5% | 0.4 | 1.0 | 1.5 | 1.8 |
|  | 1.0% | 0.4 | 0.8 | 0.9 | 1.0 |
| Bacterially-prepared chitosan media | 0.5% | 0.1 | 0.3 | 0.3 | 0.4 |
|  | 1.0% | 0.1 | 0.2 | 0.3 | 0.3 |
|  | 5.0% | 0.1 | 0.2 | 0.4 | 0.6 |
| Colloidal chitin | 0.5% | 0.4 | 0.8 | 1.4 | 1.5 |
|  | 1.0% | 0.3 | 0.7 | 0.8 | 1.7 |

To check the anti-microbial activities of the above-indicated kinds of chitosan with respect to the pathogenic microbes of the sheath blight of rice, there were prepared culture media by applying the different concentrations of colloidal chitosan, powdered chitosan, bacterially-prepared chitosan and colloidal chitin to ordinary agar media as described above, which served as the control medium. The pathogenic microbes which had been grown on a liquid medium were applied to each of the prepared culture media, and were cultured on the medium at 30° C. for one day. Thereafter, the growth conditions of colonies of the pathogenic microbes on the respective culture media were observed. It was recognized that the colonies were grown on the entire areas of the culture medium (control medium)

containing no chitosan, and the culture media containing 0.5% and 1% of powdered chitosan, 0.5% and 1% of colloidal chitin, and 0.5% and 1% of colloidal chitosan. On the culture media containing 0.5%, 1% and 5% of bacterially-prepared chitosan, on the other hand, the growth of the pathogenic microbes was remarkably restrained. No growth of the microbes was found on the culture medium containing 5% of bacterially-prepared chitosan.

It will be understood from the results of the above tests that bacterially-prepared chitosan obtained according to the present invention has excellent anti-microbial activity with respect to any of the above-indicated kinds of pathogenic microbes. This is because the bacterially-prepared chitosan having a relatively low molecular weight is more likely to be dispersed and dissolved in water than chemically-prepared chitosan, and therefore readily exhibit its anti-microbial activity. Further, since the bacterially-prepared chitosan is considered to have 40% to 50% of acetyl-group, the molecular weight of chitosan is lowered at a relatively low rate. Therefore, it appears that the occurrence of the anti-microbial effect of the bacterially-prepared chitosan can be delayed while the same effect can be provided immediately after the application of the chitosan to the diseased plants.

Another test was conducted to check an insecticidal effect of chitosan obtained according to the present invention, with respect to pine tree nematodes known as a pine weevil, which is considered a major cause for early dying of pine trees. As indicated in the graph of the accompanying drawing, when 5% of bacterially-prepared chitosan was applied to the nematodes, for example, 90% of the specimens were dead at 25° C. 5 hours after the application of the chitosan. When chemically-prepared chitosan was applied to the nematodes, on the other hand, no insecticidal effect was provided under the same conditions. It is presumed that the difference of the effects between bacterially-prepared chitosan and chemically-prepared chitosan is depending on the difference of water-dispersiblity and water-solubility between the two kinds of chitosan. In a further test, a 25% solution of culture liquid in which the present strain of bacteria (Enterobacter G-1) was cultured for two weeks was applied to the nematodes. In this case, 95% of the specimens were dead at 25° C. 5 hours after the application of the culture liquid. It is considered that the insecticidal effect of the culture liquid was provided because of the low-molecular weight chitosan and various kinds of chitinase co-existing in the culture liquid.

Still another test was conducted to check an anti-insect effect of chitosan obtained according to the present invention, with respect to a noxious insect called "rhizoctonia large patch", which usually exists in a lawn of a golf course, for example. This test was conducted by sprinkling two kinds of specimens, that is, a 100-time dilution of 5% chitosan and a 200-time dilution of 5% chitosan, on respective two 10m² test areas of lawn grass, each in an amount of 1l per m² by a watering pot. The sprinkling of the specimens was effected three times in one month, that is, Apr. 24, 1990, May 7, 1990 and May 17, 1990. The effect of the applied chitosan with respect to rhizoctonia large patches was observed two days (May 17, 1990 and May 23, 1990), and was represented by the percentage of the area in which diseased spots were present, that is, the area which was affected by the rhizoctonia large patches. The result of the above test was indicated on TABLE 3 given below, together with the result of a similar test where no chitosan was applied to the lawn grass. In the meantime, the chitosan applied as described above did no pharmaceutical harm on the lawn grass itself.

TABLE 3

| Specimen | Amount of Specimen (g,ml/m²) | Concentration Dilution (times) | Chitosan content | Diseased area (%) | Dates |
|---|---|---|---|---|---|
| Bacterially-treated chitosan | 5 | 200 | 5% | 0.1 | May 17 |
| | | | | 0.1 | May 23 |
| Bacterially-treated chitosan | 10 | 100 | 5% | 0.1 | May 17 |
| | | | | 0.1 | May 23 |
| Comparative No chitosan applied | — | — | — | 8 | May 17 |
| | | | | 6 | May 23 |

It will be understood from the results of all of the above tests that the bacterially-prepared chitosan and the culture liquid of the bacteria named Enterobacter G-1 may be practically used as a natural anti-microbial and anti-nematode agent in the agricultural field, and as a natural anti-insect agent suitably used for the lawn glass in a golf course, for example.

What is claimed is:

1. An anti-microbial composition comprising an anti-microbially effective amount of chitosan obtained by decomposing chitin with a strain of Enterobacter G-1 deposited in the Fermentation Research Institute, Agency of Industrial Science and Technology, 1-3, Higashi 1 chome, Tsukuba-shi, Ibaraki-ken, 305, Japan under deposit number FERM BP-3140 on Nov. 14, 1988 and a carrier therefor.

2. An anti-microbial composition according to claim 1, wherein said chitin is provided by a decalcified crab shell.

3. An anti-nematode composition comprising a nematode-combating effective amount of chitosan obtained by decomposing chitin with a strain of Enterobacter G-1 deposited in the Fermentation Research Institute, Agency of Industrial Science and Technology, 1-3, Higashi 1 chome, Tsukuba-shi, Ibaraki-ken, 305, Japan under deposit number FERM PB-3140 on Nov. 14, 1988 and a carrier therefor.

4. A strain of chitinolytic bacterium, named Enterobacter G-1 deposited in the Fermentation Research Institute, Agency of Industrial Science and Technology located At 1-3, Higashi 1 chome, Tsukuba-shi, Ibaraki-ken, 305, Japan, under deposit number FERM BP-3140 on the date of Nov. 14, 1988.

5. The anti-microbial composition of claim 1, wherein said chitin is decomposed in a culture containing same.

6. The anti-nematode composition of claim 3, wherein said chitin is decomposed in a culture medium containing same.

* * * * *